US00PP10439P

United States Patent [19]

Ebihara

[11] Patent Number: Plant 10,439

[45] Date of Patent: Jun. 9, 1998

[54] HYDRANGEA PLANT NAMED 'FRAU KINUE'

[75] Inventor: Hiroshi Ebihara, Ninomiya-machi, Japan

[73] Assignee: Miyoshi & Co. Ltd., Tokyo, Japan

[21] Appl. No.: 732,066

[22] Filed: Oct. 16, 1996

[51] Int. Cl.[6] ..... A01H 5/00

[52] U.S. Cl. ..... Plt./67.1

[58] Field of Search ..... Plt./67.1

[56] References Cited

U.S. PATENT DOCUMENTS

| | | | |
|---|---|---|---|
| P.P. 9,499 | 4/1996 | Ebihara | Plt./67.1 |
| P.P. 9,500 | 4/1996 | Ebihara | Plt./67.1 |
| P.P. 9,510 | 4/1996 | Ebihara | Plt./67.1 |

OTHER PUBLICATIONS

UPOVROM Disk 1997/03 Result Sheet ① GTTM UPOVROM Listing PBR HDG0021 Published Apr. 16, 1994, 1997.

*Primary Examiner*—James R. Feyrer
*Assistant Examiner*—Kent L. Bell
*Attorney, Agent, or Firm*—James R. Cypher

[57] ABSTRACT

This invention relates to a new and distinct cultivar of *Hydrangea macrophylla* (Thunb.) named 'Frau Knue' which originated as a seedling from the inventor's controlled hybridization of the *Hydrangea macrophylla* cultivars 'Crystal' and 'Silver-Edge' and is distinguished from its parents by the unique pigmentation pattern which gives a fleur-de-lis-like appearance to its florets. Sepal color of 'Frau Kinue' is approximately one half white with blue or pink pigmentation beginning at the base of the sepal and fading to white as it progresses across the length and width of the sepals. Color is deepest at the base of the sepals. The sepals of 'Crystal' are uniformly blue and the sepals of 'Silver-Edge' are uniformly red with a white edge. The new variety 'Frau Ki nue' further possesses the favorable characteristics of a compact growth habit, long lasting large flowers on a sturdy peduncle, and ability to be easily forced in a greenhouse for flowering in the spring.

1 Drawing Sheet

BACKGROUND OF THE INVENTION

This invention relates to a new and distinct cultivar of the Saxifragaceae family. The botanical name of the plant is *Hydrangea macrophylla* (Thunb.). The varietal denomination is 'Frau Kinue'. The new cultivar originated as a seedling from the inventor's controlled crossing as pollen and seed parents, respectively, the varieties known as 'Silver Edge' and 'Crystal' in Tochigi-Prefecture, Japan. 'Frau Kinue' was discovered and selected as one flowering plant within the progeny of the stated parentage in a controlled environment. This new cultivar has been successfully asexually reproduced by vegetative cuttings under controlled environmental conditions at a commerical nursery in Tochigi-Prefecture, Japan, under the direction of the inventor over a ten year period from 1986 to 1996, with its distinguishing characteristics remaining stable.

'Frau Kinue' is distinguished from its parents and all other varieties of Hydrangea of which I am aware by the pigmentation in its sepals which is approximately half white and half colored with the color radiating out from the base of each sepal near the center of the floret to give a fluer-de-lis-like appearance to the florets. Sepal color of 'Frau Kinue' is white with blue or pink pigmentation. Sepal pigmentation of individual *Hydrangea macrophylla* plants depends on the nutrients and pH of the growing medium. The unique pigmentation pattern which gives the new cultivar a pink and white, or blue and white, flower is created by the sepals being colored at the base near the center of the floret and white at the edges. The base of the sepals near the center of the floret is darkest in pigmentation; the pigmentation gradually spreading across the length and width of the sepal and shading to a lighter color finally disappearing into the white edges of the sepals. This gives each floret the appearance of being white with four pink or blue fans radiating out from the base of the floret. The appearance of the total florescence is that of approximately a half colored, half white flower having an unusual fluer-de-lis-like pigmentation pattern.

The sepal coloration of the seed parent 'Crystal' is uniformly blue. The sepals of the pollen parent 'Silver Edge' are uniformly red except for white edges.

While there are other *Hydrangea macrophylla* plants with a coloration pattern in their sepals, none of the other known varieties have the particular pattern of the 'Frau Kinue.' The variety of plant closest in characteristics to 'Frau Kinue' of which I am aware, is the cultivar'Frau Machiko.' The parents of 'Frau Machiko' are *Hydrangea macrophylla (Thunb) 'Silver Edge' and Hydrangea macrophylla* (Thunb) 'Madam Blumkock,' seed and pollen parents respectively. 'Frau Machiko' has a pigmentation pattern similar to the new cultivar in that the pigmentation radiates out from the base of the sepals disappearing to white, but the new cultivar is distinguished from 'Frau Machiko' in the following ways: 'Frau Kinue' is a smaller plant overall having smaller florets (approximately one half the size of the florets of'Frau Machiko'); much fewer number of florets per inflorescence resulting in a less dense appearance; inflorescence shape is less spherical and more flat; sepals are significantly more rounded with less tapering at the base and apex; sepals are flat, not ruffled or wavy; and the pigmentation pattern covers—a much larger area of the sepals. The new variety of Hydrangea as described herein is further characterized by its compact growth habit, the ease with which it can be forced in a greenhouse, and its large, long lasting flowers that do not need to be staked, which make it desirable for pot culture.

DESCRIPTION OF THE DRAWINGS

The accompanying drawings consist of color photographs that show the typical plant form, including the inflorescence, foliage, and unique sepal pigmentation pattern. 'Frau Kinue' is shown with a pink and white sepal pigmentation pattern, but a blue and white pigmentation pattern is also possible by maniuplation of the nutrient amendments and the pH of the growing medium. The colors are represented as truly as possible using conventional photographic procedures.

DESCRIPTION OF THE NEW PLANT

Figure 1:
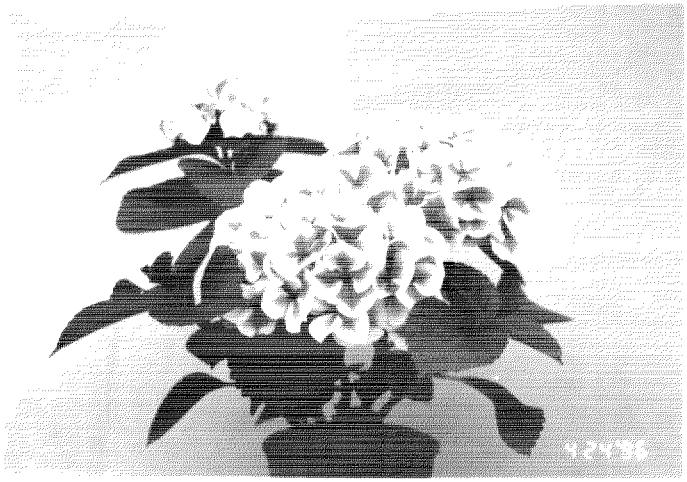
FIG. 1 is a view of the entire plant showing its form, compact growth habit, dark green foliage, inflorescence, and unique sepal pigmentation pattern which gives a fleur-de-lis-like appearance to the florets.
Figure 2:
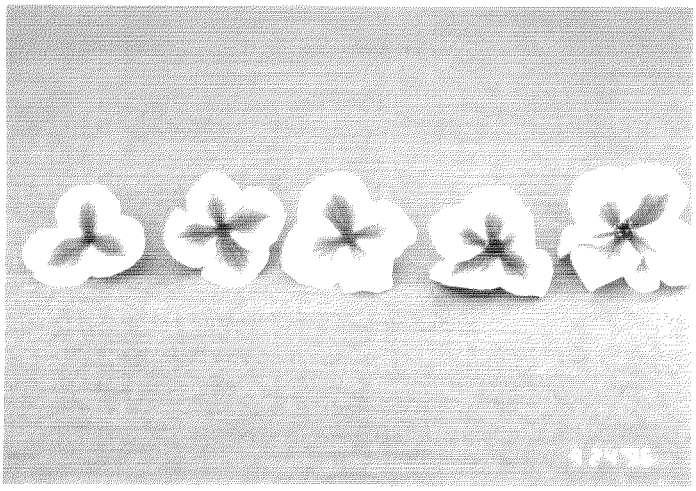
FIG. 2 is a close-up view of the illustrating the unique color pigmentation pattern, round sepal shape, and smooth edges.
Figure 3:
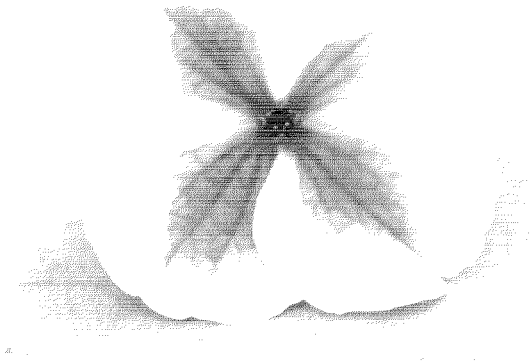
FIG. 3 is a close-up view of one floret illustrating the half colored, half white unique pigmentation pattern of the sepals, round shape, flat not ruffled shape, and smooth edge.

'Frau Kinue' has not been observed under all possible environmental conditions. The phenotype may vary significantly with varations in environment such as temperature, light intensity and day-length. The following is a detailed description of the new cultivar as forced under the prevailing day-lengths at Half Moon Bay, Calif. under commercial greenhouse conditions at a time appropriate for the sale of the cultivar in the spring. The color determinations were made with The Royal Horticultural Society (R.H.S.) Colour Chart.

The Plant

Orgin: Seedling.

Parentage:

*Seed parent.*—*Hydrangea macrophylla* (Thunb) 'Crystal'.

*Pollen parent.*—*Hydrangea macrophylla* (Thunb) 'Silver Edge'.

Classification:

*Botanic.*—*Hydrangea macrophylla* (Thunb.) 'Frau Kinue'.

*Commerical.*—Florist Hydrangea 'Frau Kinue'.

Form: Upright, compact shrub.

Height: Flowering shoots reach 25½ cm. in a 4" pot.

Growth: Upright, vigorous growth habit; when forced to bloom in greenhouse the addition of growth regulators is necessary to control height.

Flowerhead: Terminal; composite rounded clusters of small florets but not highly dome-shaped or extremely dense; composed of florets carried on sturdy penuncles.

Stems: Colorless lenticels; lateral buds are reddish; reddish coloration above and below leaf attachment sites.

Foliage: Abundant.

*Size of leaf.*—As large as 80 mm wide by 109 mm long.

*Shape of leaf.*—Elliptic with acute base and apex; margins are serrate.

*Texture.*—Glabrous; veins dominate on the underside of the leaf and are sunken on the leaf surface.

*Color.*—*Upper side is R.H.S.* 137 A (green group); under side is R.H.S. 137 D (green group); veins are R.H.S. 145D (yellow-green group).

*Petioles.*—20 mm long.

The Bud

Form: Globose; with 4 to 5 connate petals. Buds in the very center of the inflorescence are non-sepalous. The majority of buds have sepals.

Size: 3 mm.

Aspect: Smooth.

Rate of opening: Buds with sepals opening more slowly than buds without sepals.

Color: Early green stage is R.H.S. 150 D (yellow-green group). Mature stage is R.H.S. 87D violet group.

Arrangement: Borne on 5 branched panicles.

Infloresecence

Time of blooming: Forced in approximately 80 days at 19° C night temperatures.

Form: Paniculate. Both sterile, sepalous florets and fertile, non-sepalous florets borne on same panicle.

Size of Inflorescence: Individual inflorescence size is dependent on the number of inflorescences per plant. The large inflorescences have been measured with a 14 cm diameter, an an 40.64 cm. circumference on a 4 bloom plant. Usually 14 cm diameter on a 3 +boom plant.

Shape: Spherical clusters of small florets; sepalous florets are flat and overlap one another. Sepals are persistent. Sepals elongate and mature as the inflorescence matures. Non-sepalous, florets are inconspicuous and hidden by sepalous florets. The inflorescence is dense.

Appearance: Showy.

Persistence: 4 or more weeks.

Fragrance: Faintly sweet.

Fruit: None.

Reproductive organs:

*Stamens.*—8 to 10 stamens present, usually 8. Pollen is white.

*Stigma.*—2–3 pronged stigma, usually 2.

Sepalous florets:

*Number of sepals.*—3 to 5 sepals per floret, usually 4.

*Aspect of sepals.*—smooth.

*Shape of sepals.*—Broad, more round than reinform; tapering slightly at the base and apex which has one small notch; flat—not wavy; smooth edge—not serrated; more wide than long.

*Size of sepals.*—Sepals of almost equal size; not much difference in size in a four sepal floret (less than 1 cm. difference); slightly more difference in a 5 sepaled floret. The largest sepal measured 30 mm wide by 26 mm long.

*Size of one large 4 petaled floret.*—49 mm. wide by 51 mm. long.

*Coloration of sepals.*—Approximately half white and half colored pink or blue, with the color radiating out like a fan from the base of the sepal at the center of the floret and disappearing into the white edges of the sepals. Sepal color varies from pink to blue according to the soil pH and nutrional amendments supplied. The amount of white varies somewhat depending upon the age and location within the flower. The white edge usually is from 5 to 10 mm wide.

Middle: 64C Red Purple Group.

Edge: 155D White Group.

I claim:

1. A new and distinct hybrid plant variety of Saxifragaceae family substanitially as herein shown and described.

* * * * *